United States Patent [19]

Connor et al.

[11] 4,179,447
[45] Dec. 18, 1979

[54] PROCESS FOR THE PRODUCTION OF 2-SUBSTITUTED CHROMONES

[75] Inventors: David T. Connor, Ann Arbor, Mich.; Patricia A. Young, Madison, N.J.; Max von Strandtmann, New Castle, Del.

[73] Assignee: Warner-Lambert Company, Morris Plains, N.J.

[21] Appl. No.: 964,998

[22] Filed: Nov. 30, 1978

Related U.S. Application Data

[63] Continuation of Ser. No. 816,122, Jul. 15, 1977, abandoned.

[51] Int. Cl.² .................................... C07D 311/22
[52] U.S. Cl. ............................................ 260/345.2
[58] Field of Search .................................. 260/345.2

[56] References Cited

U.S. PATENT DOCUMENTS

| | | | |
|---|---|---|---|
| 3,699,128 | 10/1972 | Strandtmann et al. | 260/345.2 |
| 3,850,966 | 11/1974 | Cohen et al. | 260/345.2 |

*Primary Examiner*—Nicky Chan
*Attorney, Agent, or Firm*—Albert H. Graddis

[57] ABSTRACT

This invention is concerned with a novel process for the production of 2-substituted chromones (I) from readily available 4-methoxycoumarins.

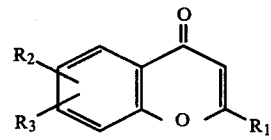

These compounds are useful as antiallergy agents.

3 Claims, No Drawings

PROCESS FOR THE PRODUCTION OF 2-SUBSTITUTED CHROMONES

This is a continuation of application Ser. No. 816,122 filed July 15, 1977, now abandoned.

The present invention relates to a novel process. More particularly, the present invention relates to the production of 2-substituted chromones of the formula:

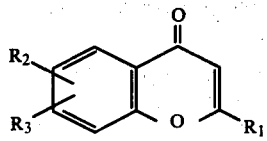

wherein $R_1$ is (methylsulfinyl)methyl, acetyl(methylthio)methyl, dimethoxymethyl, formyl or hydroxymethyl; $R_2$ and $R_3$ are hydrogen, halogen, lower alkyl, lower alkoxy or hydroxy.

2-Substituted chromones are useful as antiallergy agents. Thus, for example, 2-formylchromones are readily converted by standard techniques to chromone-2-carboxylic acids and 2-(5-tetrazolyl) chromones, which are known antiallergy agents. See, also, G. P. Ellis and G. Barker, in "Progress in Medicinal Chemistry," Vol. 9, G. P. Ellis and G. B. West, Eds., American Elsevier Publishing Co., Inc., New York, N.Y., 1973, p. 65.

In addition, the 2-hydroxymethylchromones are active in the prevention of allergic and asthmatic reactions in rats at dose levels of 0.5 mg/kg to 100 mg/kg; thus, 2-(hydroxymethyl)-4H-1-benzopyran-4-one shows a 23% inhibition of the allergic response at 0.5 mg/kg when tested intravenously in the passive cutaneous anaphalaxis (PCA) screen, which is a modification of procedures described by I. Mota, Life Sciences, 7:465 (1963) and Z. Ovary and O. Bier, Proc. Soc. Exptl. Biol. Med., 81:585 (1952). Consequently, they are indicated in the management of asthma, hay fever and other allergic conditions in the above dose range.

It has now been found that the above compound I can be prepared from readily available 4-methoxycoumarins, in a manner described below.

The starting 4-methoxycoumarin of the formula:

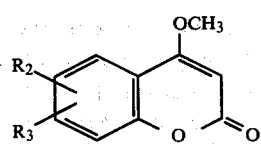

is prepared by the method described in "Reagents for Organic Synthesis" by L. F. Fieser and M. Feiser, J. Wiley and Sons, Inc., New York, N.Y., p. 295 (1967) or by the method described in Example 12 of the instant specification.

Treating compound II with sodium methylsulfinylmethide yields 2-(methylsulfinylmethyl) chromone of the formula:

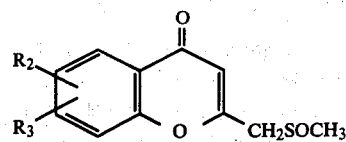

In the next step, compound III is refluxed with acetic anhydride which gives 2[acetoxy(methylthio)methyl]-chromone of the formula:

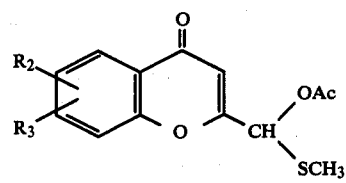

Compound IV is converted to 2-(dimethoxymethyl)-chromone:

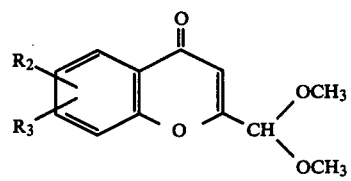

by refluxing in methanol with iodine.

Compound V, under acid hydrolysis conditions, yields 2-formyl chromone of the formula:

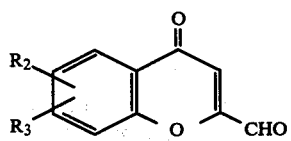

Reduction of VI with a complex metal hydride such as sodium borohydride gives 2-hydroxymethyl chromone of the formula:

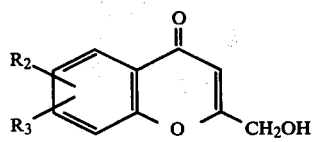

The foregoing compounds are useful as intermediates, as described in the above reaction sequence. The aldehyde substituted compounds are intermediates for chromone-2-carboxylic acids.

To further illustrate the practice of this invention, the following examples are included:

EXAMPLE 1

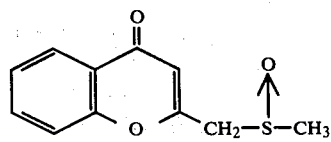

2-[Methylsulfinyl)methyl]-4H-1-benzopyran-4-one

A mixture of dimethyl sulfoxide (500 ml), benzene (375 ml) and sodium hydride (52 g of a 57% oil dispersion, 1.24 mole), was heated at 75° under nitrogen until all the solid dissolved giving a clear gray-green solution. The solution was cooled in an ice-bath and 4-methoxycoumarin (75g, 0.425 mole) was added. The reaction mixture was stirred at room temperature for one hour and poured into excess anhydrous ether. The ether was decanted from the insoluble salts, which were washed several times with fresh ether. The salts were dissolved in a minimum of cold water and acidified with ice-cold 5 N hydrochloric acid. The acidified solution was extracted with chloroform (5×40 ml). The extracts were combined, dried over Na₂SO₄, and evaporated at reduced pressure to give a solid product. Recrystallization from absolute ethanol gave white crystals (57.3 g, 61%), m.p. 142°–146°.

Anal. Calcd. for $C_{11}H_{10}O_3S$: C, 59.44; H, 4.54; S, 14.43. Found: C, 59.05; H, 4.46; S, 14.16.

EXAMPLE 2

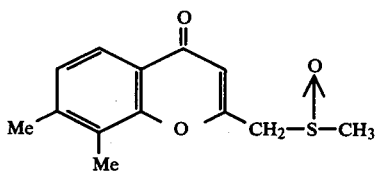

7,8-Dimethyl-2-[(methylsulfinyl)methyl]-4H-1-benzopyran-4-one

Prepared by the method described for Example 1 from 7,8-dimethyl-4-methoxy-2H-1-benzopyran-2-one (8.0 g 0.04 m). The crude product precipitated out of solution on acidification of the aqueous fraction. Recrystallization from absolute ethanol gave off-white crystals (4.4 g, 45%), m.p. 205°–209°.

Anal. Calcd. for $C_{13}H_{14}O_3S$: C, 62.38; H, 5.64; S, 12.81. Found: C, 62.57; H, 5.75; S, 12.74.

EXAMPLE 7

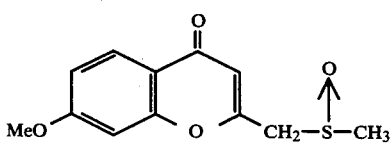

7-Methoxy-2-[(methylsulfinyl)methyl]-4H-1-benzopyran-4-one

Prepared by the method described for Example 1 from 4,7-dimethoxy-2H-1-benzopyran-2-one (25 g 0.12 m). Recrystallization from absolute ethanol gave pale-pink crystals (21 g, 69%), m.p. 157°–159°.

Anal. Calcd. for $C_{12}H_{12}O_4S$: C, 57.13; H, 4.79; S, 12.71. Found: C, 57.09; H, 4.87; S, 12.54.

EXAMPLE 4

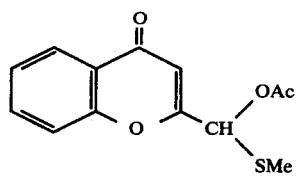

2-[(Methylthio)hydroxymethyl]-4H-1-benzopyran-4-one acetate

A solution of 2-[(methylsulfinyl)methyl]-4H-1-benzopyran-4-one (2.22 g, 0.01 m) in acetic anhydride (15 ml) was refluxed under nitrogen for 5 hours. The solvent was removed under reduced pressure to give a brown gum, which crystallized on standing. Recrystallization from methanol gave off-white crystals (2.36 g, 90%), m.p. 123°–125°.

Anal. Calcd. for $C_{13}H_{12}O_4S$: C, 59.08; H, 4.58; S, 12.13. Found: C, 59.04; H, 4.60; S, 12.06.

EXAMPLE 5

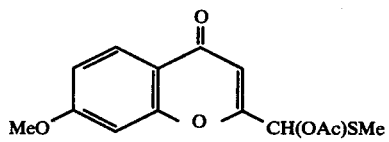

7-Methoxy-2-[(methylthio)hydroxymethyl]-4H-1-benzopyran-4-one acetate

Prepared by the method described for Example 4 from 7-methoxy-2-[(methylsulfinyl)methyl]-4H-1-benzopyran-4-one (15.0 g 0.0595 m). Recrystallization from ethyl acetate gave beige colored crystals (13.2 g, 75%), m.p. 136°–138°.

Anal. Calcd. for $C_{14}H_{14}O_5S$: C, 57.13; H, 4.80; S, 10.89. Found: C, 57.21; H, 4.82; S, 11.11.

EXAMPLE 6

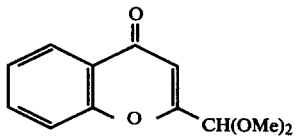

2-(Dimethoxymethyl)-4H-1-benzopyran-4-one

A stirred solution of 2-[(methylthio)hydroxymethyl)-4H-1-benzopyran-4-one acetate](2.64 g, 0.01 m) and iodine (1.39 g, 0.01 m) in methanol (50 ml) was refluxed under nitrogen for 6 hours. After cooling, the solvents were removed under reduced pressure. The red-brown oil was dissolved in chloroform and washed three times (30 ml) with aqueous saturated sodium thiosulfate. The chloroform extract was dried over sodium sulfate. Removal of the solvent under reduced pressure gave crude solid product. Recrystallization from isopropyl ether gave yellow crystals (1.9 g, 86%), m.p. 64°–68°.

Anal. Calcd. for $C_{12}H_{12}O_4$: C, 65.44; H, 5.49. Found: C, 64.91; H, 5.36.

EXAMPLE 7

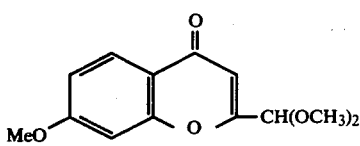

7-Methoxy-2-(dimethoxymethyl)-4H-1-benzopyran-4-one

Prepared by the method described for Example 6 from 7-methoxy-2-[(methylthio)hydroxymethyl]-4H-1-benzopyran-4-one acetate (6.5 g, 0.022 m). Recrystallization from methyl ethyl ketone gave pale pink crystals (4.1 g, 74%), m.p. 99°–101°.

Anal. Calcd. for $C_{13}H_{14}O_5$: C, 62.39; H, 5.64. Found: C, 62.15; H, 5.64.

EXAMPLE 8

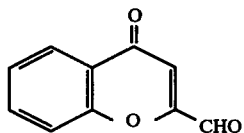

4H-1-Benzopyran-4-one-2-carboxaldehyde

A stirred solution of 2-(dimethoxymethyl)-4H-1-benzopyran-4-one (1.1 g, 0.005 m) in 5 N hydrochloric acid (20 ml) was heated at 100° for 3 hours. The reaction mixture was cooled and extracted with $CHCl_3$. The extracts were dried over $MgSO_4$ and evaporated under reduced pressure to give a crystalline product. Recrystallization from ethyl acetate gave off-white crystals (710 mg, 81%), m.p. 159°–161°.

Anal. Calcd. for $C_{10}H_6O_3$: C, 68.96; H, 3.47. Found: C, 68.56; H, 3.57.

EXAMPLE 9

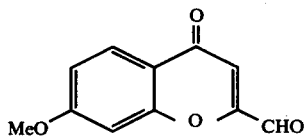

7-Methoxy-4H-1-benzopyran-4-one-2-carboxaldehyde

Prepared by the method described for Example 8 from 7-methoxy-2-(dimethoxymethyl)-4H-1-benzopyran-4-one (3.5 g, 0.014 m). Recrystallization from ethyl acetate gave off-white crystals (200 mg), m.p. 175°–177°.

Anal. Calcd. for $C_{11}H_8O_4$: C, 64.70; H, 3.95. Found: C, 64.47; H, 4.08.

EXAMPLE 10

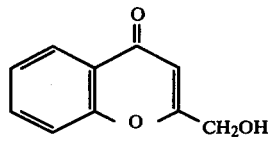

2-(Hydroxymethyl)-4H-1-benzopyran-4-one

A mixture of 4H-1-benzopyran-4-one-2-carboxaldehyde (400 mg, 0.0023 m) and sodium borohydride (8.8 mg. 0.0023 m) in methanol (20 ml) was stirred at room temperature for 30 minutes. The solvent was removed at reduced pressure to give a white solid. The solid was washed with water, sucked dry, and recrystallized from ethanol to give white crystals (220 mg, 55%), m.p. 165°–167°.

Anal. Calcd. for $C_{10}H_8O_3$: C, 68.18; H, 4.58. Found: C, 67.95; H, 4.62.

EXAMPLE 11

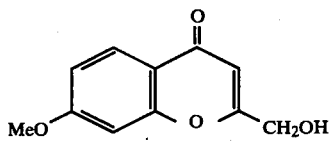

7-Methoxy-2-(hydroxymethyl)-4H-1-benzopyran-4-one

Prepared by the method described for Example 10 from 7-methoxy-4H-1-benzopyrano-4-one-2-carboxaldehyde (150 mg., 0.000735 m). Recrystallization from methanol gave white crystals (45 mg, 30%), m.p. 182°–183°.

Mass Spectrum

| Observed molecular ion | 206.0653 |
|---|---|
| Calculated for $C_{11}H_{10}O_4$ | 206.0579 |

EXAMPLE 12

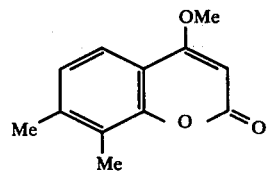

7,8-Dimethyl-4-methoxy-2H-1-benzopyram-2-one

Excess diazomethane in ether was added slowly to a solution of 7,8-dimethyl-4-hydroxy-2H-1-benzopyran-2-one (28.0 g, 0.147 m) in ether (100 ml). After the vigorous reaction bubbling ceased, the reaction was stirred an additional hour. The ether was removed under reduced pressure to give solid product (7.0 g, 23.4%), m.p. 150°–155°.

We claim:

1. 7,8-dimethyl-2-[(methylsulfinyl)methyl]-4H-1-benzopyran-4-one.
2. 2-[(methyl-sulfinyl)methyl]-4H-1-benzopyran-4-one.
3. 7-methoxy-2-[(methylsulfinyl)methyl]-4H-1-benzopyran-4-one.

* * * * *